US012590286B2

(12) United States Patent
Lee

(10) Patent No.: US 12,590,286 B2
(45) Date of Patent: Mar. 31, 2026

(54) METHOD FOR PREPARING AGENT FOR PREVENTION OF HAIR LOSS AND PROMOTION OF HAIR REGROWTH THROUGH FUSION FERMENTATION OF LACTIC ACID BACTERIA

(71) Applicants: Chae Kun Lee, Hwaseong-si (KR); KB&H Co., Ltd., Namyangju-si (KR)

(72) Inventor: Chae Kun Lee, Hwaseong-si (KR)

(73) Assignees: Chae Kun Lee, Hwaseong-si (KR); KB&H Co., Ltd., Namyangju-si (KR)

( * ) Notice: Subject to any disclaimer, the term of this patent is extended or adjusted under 35 U.S.C. 154(b) by 394 days.

(21) Appl. No.: 18/212,190

(22) Filed: Jun. 21, 2023

(65) Prior Publication Data
US 2023/0348844 A1 Nov. 2, 2023

Related U.S. Application Data

(63) Continuation of application No. PCT/KR2021/019416, filed on Dec. 20, 2021.

(30) Foreign Application Priority Data

Dec. 23, 2020 (KR) ........................ 10-2020-0182351

(51) Int. Cl.
| | |
|---|---|
| *C12N 1/20* | (2026.01) |
| *A61K 8/99* | (2017.01) |
| *A61Q 7/00* | (2006.01) |
| *C12N 1/18* | (2026.01) |
| *A61K 35/744* | (2015.01) |
| *C12R 1/01* | (2006.01) |
| *C12R 1/865* | (2006.01) |

(52) U.S. Cl.
CPC .................. *C12N 1/20* (2013.01); *A61K 8/99* (2013.01); *A61Q 7/00* (2013.01); *C12N 1/18* (2013.01); *A61K 35/744* (2013.01); *A61K 2800/85* (2013.01); *C12R 2001/01* (2021.05); *C12R 2001/865* (2021.05)

(58) Field of Classification Search
CPC ... C12N 1/20; C12N 1/18; A61K 8/99; A61K 35/744; A61K 2800/85; A61Q 7/00; C12R 2001/865
See application file for complete search history.

(56) References Cited

FOREIGN PATENT DOCUMENTS

| KR | 10-2013-0026127 | A | | 3/2013 | |
|---|---|---|---|---|---|
| KR | 20150054094 | A | * | 5/2015 | ............. A61Q 5/006 |
| KR | 10-2016-0070508 | A | | 6/2016 | |
| KR | 101704645 | B1 | * | 2/2017 | ............. A23L 7/104 |
| KR | 10-2017-0100828 | A | | 9/2017 | |
| KR | 20180063678 | A | * | 6/2018 | ............. A61K 8/97 |
| KR | 10-2019-0011042 | A | | 2/2019 | |
| KR | 10-2075842 | B1 | | 2/2020 | |

OTHER PUBLICATIONS

Bottacini et al. "Diversity, ecology and intestinal function of bifidobacteria." Microb Cell Fact 13 (Suppl 1), S4 (2014). https://doi.org/10.1186/1475-2859-13-S1-S4 (Year: 2014).*
English Translation of KR-20150054094-A. 15 pages total. Available May 20, 2015. (Year: 2015).*
English Translation of KR-101704645-B1. 21 pages total. Available Feb. 8, 2017. (Year: 2017).*
English Translation of KR-20180063678-A. 13 pages total. Available Jun. 12, 2018 (Year: 2018).*
International Search Report for PCT/KR2021/019416 mailed Apr. 4, 2022 from Korean Intellectual Property Office.

* cited by examiner

*Primary Examiner* — Anand U Desai
*Assistant Examiner* — Andrew T Moehlman
(74) *Attorney, Agent, or Firm* — Revolution IP, PLLC

(57) ABSTRACT

The present invention is characterized by implementation of a method for preparing an agent for prevention of hair loss and promotion of hair regrowth wherein aerobic lactic acid bacteria and anaerobic lactic acid bacteria are fermented in a fusion manner to repeat a cycle of fermentation, degradation, and synthesis whereby the prevention of hair loss and the promotion of hair regrowth are achieved through the fusion fermentation process of lactic acid bacteria.

4 Claims, 2 Drawing Sheets

【Figure 1】
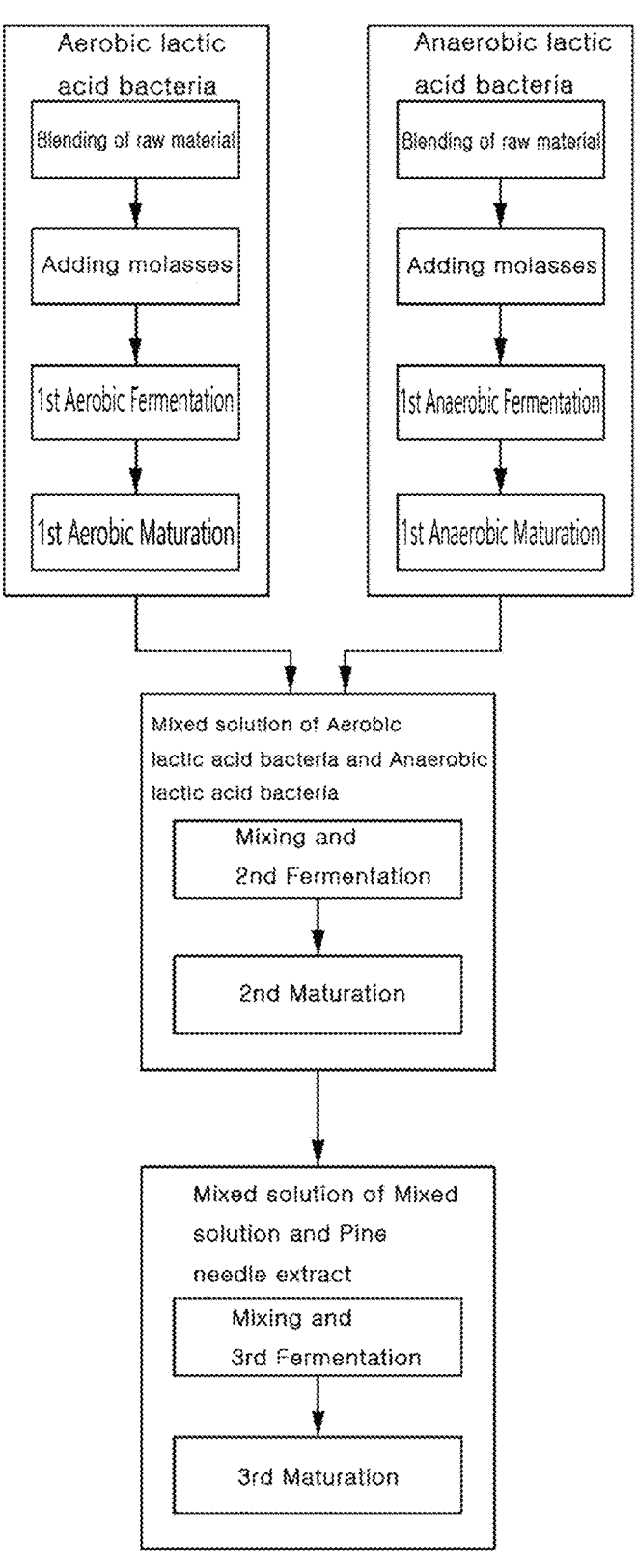

【Figure 2】
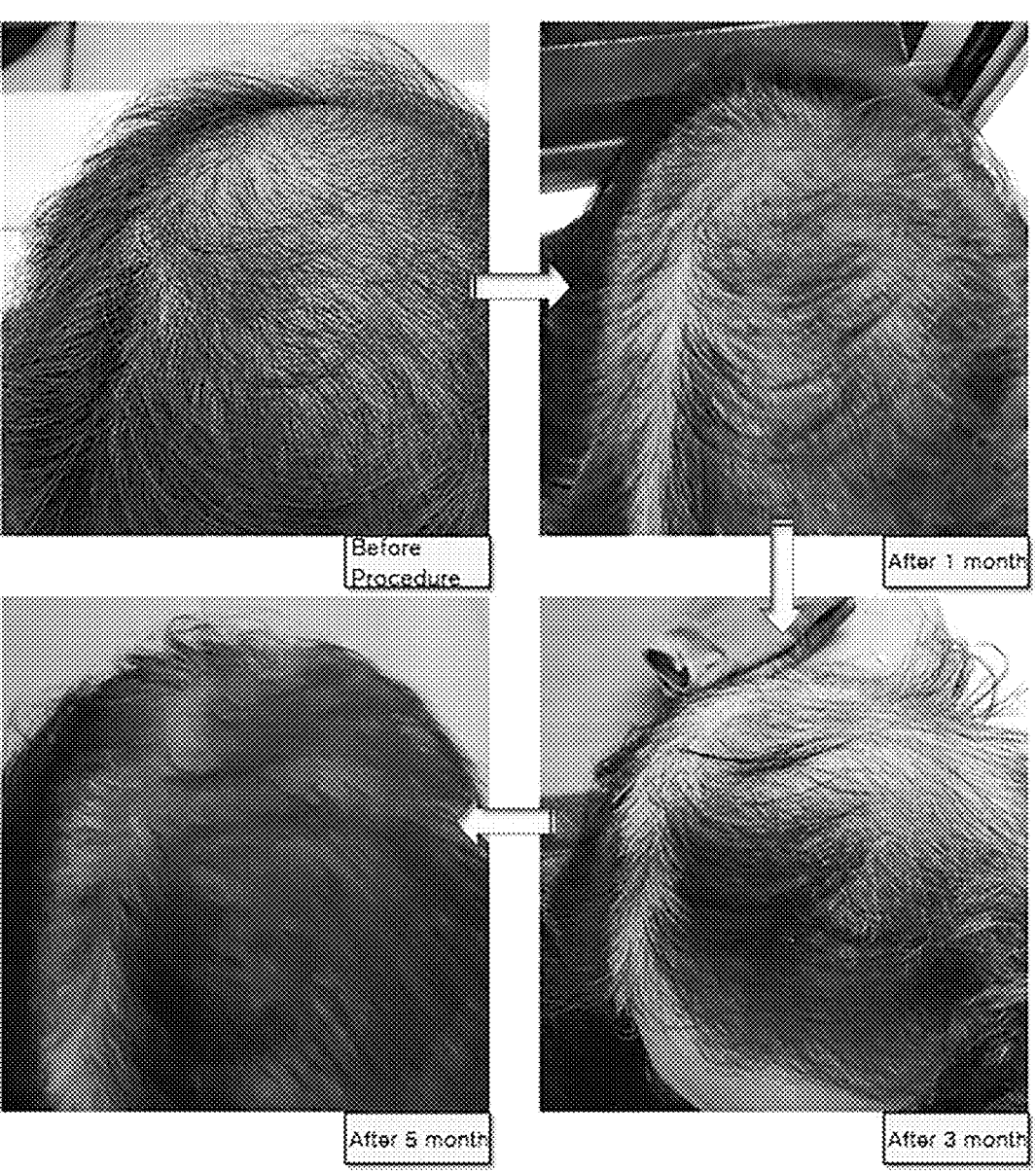

METHOD FOR PREPARING AGENT FOR PREVENTION OF HAIR LOSS AND PROMOTION OF HAIR REGROWTH THROUGH FUSION FERMENTATION OF LACTIC ACID BACTERIA

TECHNICAL FIELD

The present invention relates to a method for preparing an agent for prevention of hair loss and promotion of hair regrowth, and more specifically, to a method for preparing an agent for prevention of hair loss and promotion of hair regrowth through a fusion fermentation process of lactic acid bacteria.

BACKGROUND ART

In general, alopecia (hair loss) is a condition in which there is no hair where hair should normally be, and hair does not have a physiological function directly related to life. However, hair plays a very important role cosmetically. In addition, hair has functions such as UV protection and head protection. Severe hair loss can cause problems in social life and can have a serious psychological impact, so it is important in terms of quality of life.

Hair is produced in hair follicles, and hair follicles periodically go through an active phase and a stationary phase. The temporal interval of the hair cycle varies depending on the body part. In the case of hair on the head, it goes through a anagen phase (growth phase) of about 26 years and a catagen phase of 2 to 4 weeks, followed by a telogen period (rest phase) of about 3 to 4 months. Each hair follicle has 10 to 20 hair follicle growth cycles in its lifetime. In addition, as a type of hair, there are lanugo hair covered in the fetus, vellus hair on the skin of children, intermediate hair, and terminal. Factors involved in hair growth include genetic factors, androgens, which are male hormones, polypeptide growth factors, neuropeptides, and the like.

Hair loss can be clinically divided into cicatricial alopecia with scarring and non-cicatricial alopecia with only hair loss. The cicatricial alopecia is a disease in which hair follicles are destroyed and hair does not regrow. A normal person has about 100,000 hairs. The hairs of a normal person grow at an average of 0.37 mm per day, and grow by about 1 cm per month. Generally, 85 to 90% of hair grows in the anagen phase, and the number of anagen hair follicles decreases with age. Therefore, 10 to 15% of hair follicles are in the catagen or telogen phase, and an average of 50 to 60 hairs are lost per day. This amount of hair loss is normal, but if more than 100 hairs are lost per day, alopecia should be suspected.

In addition, hair loss in the fall is due to the fact that the hair suffered from strong sunlight and excessive scalp secretion during the summer loses a large amount over time, and it is also caused by the temporary increase in the secretion of male hormones that affect hair loss in the fall. For the treatment of hair loss, oral administration of finasteride (finasteride), topical application of minoxidil, hair transplant surgery and the like have become major treatments.

As a prior art related to the applied invention, the manufacturing method of natural hair restorer is disclosed to comprise: a step of processing a first mixed solution containing 10 to 30 parts by weight of *Colocasia esculenta* nano-powder and 70 to 90 parts by weight of Rhynchosia nolubilis nano-powder (S110); a step of extracting an extract by fermenting the first mixed solution using lactic acid bacteria (S120); a step of preparing a second mixed solution by mixing the extract and distilled water at a ratio of 2:1 (S130); a step of first filtering the second mixed solution after stirring thereof (S140); and a step of obtaining a fermented nano-product from the first filtrate prepared in the step S140 (S150). In addition, as lactic acid bacteria, *Bifidobacterium longum* and *Bifidobacterium adolescentis* of the genus *Bifidobacterium* or *Lactobacillus acidophilus, Lactobacillus lactis* and *Lactobacillus cremoris* in the genus *Lactobacillus* are disclosed, and the fermented nano-product is disclosed to be composed of oligosaccharide, vitamins, amino acids, anthocyanin, organic acids, bacteriocin, γ-oryzanol, and other mucilages. The restorer of prior art have low extraction efficiency from ingredients, insufficient fermentation and maturation of lactic acid bacteria, so that hair regrowth by active ingredients cannot be sustained, and safety problems have been pointed out because they can cause irritation or inflammation to the scalp.

DISCLOSURE

Technical Problem

The present invention is intended to solve the above problems, it is objected to prevent the progression of hair loss and promote hair regrowth without causing inflammation on the skin and any side effects on the human body by preparing an agent for prevention of hair loss and promotion of hair regrowth by sufficiently repeating cycles of fermentation, decomposition, and synthesis through fusion fermentation of aerobic lactic acid bacteria and anaerobic lactic acid bacteria.

Technical Solution

In order to achieve the above object, the present invention is characterized by providing a method for preparing an agent for prevention of hair loss and promotion of hair regrowth through fusion fermentation of lactic acid bacteria, which comprises: (a) a step of blending aerobic lactic acid bacteria raw materials by blending *Lactobacillus*-genus 40 to 60 parts by weight and *Saccharomyces cerevisiae* 40 to 60 parts by weight, and diluting the blended raw materials with water where the blended raw materials are diluted to be 1 to 10 parts by weight based on the total amount with water; (b) a step of adding molasses into the aerobic lactic acid bacteria raw materials, where the molasses solution prepared by diluting 100 to 300 g of the molasses with 10 L of water is blended with the aerobic lactic acid bacteria raw materials; (c) a step of $1^{st}$ fermentation to prepare an aerobic lactic acid bacteria $1^{st}$ culture solution by fermenting the aerobic lactic acid bacteria raw materials blended with molasses at 15 to 35° C. for 10 to 15 days while introducing air thereto in an amount of 20 to 40 parts by weight per minute based on the total content of the aerobic lactic acid bacteria raw materials blended with molasses; (d) a step of a $1^{st}$ maturation to mature the aerobic lactic acid bacteria $1^{st}$ culture solution in a sealed state at 15 to 35° C. for 10 to 15 days; (e) a step of blending anaerobic lactic acid bacteria raw materials by blending *Weissella* sp 40 to 60 parts by weight and *Bifidobacterium* 40 to 60 parts by weight, and diluting the blended raw materials with water where the blended raw materials are diluted to be 1 to 10 parts by weight based on the total amount with water; (f) a step of adding molasses into the anaerobic lactic acid bacteria raw materials, where the molasses solution prepared by diluting 1 to 3 kg of the molasses with 10 L of water is blended with the anaerobic lactic acid bacteria raw materials; (g) a step of $1^{st}$ fermentation to prepare an anaerobic lactic acid bacteria $1^{st}$ culture solution by fermenting the anaerobic lactic acid bacteria raw materials blended with molasses at 15 to 35° C. for 10 to 15 days while introducing air thereto in an amount of 20 to 40 parts by weight per minute based on the total content of the anaerobic lactic acid bacteria raw materials blended with molasses; (h) a step of a $1^{st}$ maturation to mature the anaerobic lactic acid bacteria $1^{st}$ culture solution in a sealed state at 15 to 35° C. for 10 to 15 days; (i) a step of a $2^{nd}$ fermentation to prepare a $3^{rd}$ culture solution by mixing the $1^{st}$ matured aerobic lactic acid bacteria $1^{st}$ culture solution and the $1^{st}$ matured anaerobic lactic acid bacteria $1^{st}$ culture solution, blending the mixed solution with a molasses solution prepared by diluting 0.5 to 1.5 kg of molasses with 10 L of water, and with the mixed solution, and fermenting the mixed solution blended with the diluted molasses solution at 25 to 45° C. for 10 to 15 days while introducing air thereto in an amount of 20 to 40 parts by weight per minute based on the total content of the mixed solution blended with the diluted molasses solution; and (j) a step of a $2^{nd}$ maturation to mature the fermented $2^{nd}$ culture solution in a sealed state at 25 to 45° C. for 10 to 15 days.

In addition, the present invention may further comprises: (k) a step of a $3^{rd}$ fermentation to prepare a $3^{rd}$ culture solution by mixing the secondarily matured $2^{nd}$ culture solution and a fermented pine needle extract solution prepared by diluting 0.1 to 1 kg of a pine needle extract with 10 L of water based on the $2^{nd}$ culture solution and then fermenting thereof, and fermenting the $2^{nd}$ culture solution mixed with the fermented pine needle extract solution at 38 to 42° C. for 10 to 15 days while introducing air thereto in an amount of 10 to 20 parts by weight per minute based on the total content of the $2^{nd}$ culture solution mixed with the fermented pine needle extract solution; and (1) a step of a $3^{rd}$ maturation to mature the fermented $3^{rd}$ culture solution in a sealed state at 38 to 42° C. for 10 to 15 days.

In addition, in the present invention, the fermented pine needle extract solution may be prepared by mixing a pine needle extract 40 to 60 parts by weight and molasses 40 to 60 parts by weight and maturing in a sealed state at 15 to 35° C. for 120 to 180 days.

In addition, the present invention is characterized by providing an agent for prevention of hair loss and promotion of hair regrowth by fusion fermentation of lactic acid bacteria prepared by the above method.

Advantageous Effects

According to the present invention repeating cycles of fermentation, decomposition, and synthesis through fusion fermentation of aerobic lactic acid bacteria and anaerobic lactic acid bacteria, by maximizing active ingredients for preventing hair loss and promoting hair regrowth, it prevents hair from falling off the scalp or hair becoming sparse or thinning when applied to the scalp, and prevents side effects that cause scalp troubles by fermented and aged lactic acid bacteria mixed solution. Therefore, there is an advantage in implementing the growth of healthy hair by promoting the delay of the hair cycle from the anagen phase to the catagen phase.

DESCRIPTION OF DRAWINGS

FIG. 1 is a flowchart showing the method for preparing an agent for prevention of hair loss and promotion of hair regrowth through fusion fermentation of lactic acid bacteria as an example according to the present invention.

FIG. 2 is a photograph showing the result of applying the agent for prevention of hair loss and promotion of hair regrowth through fusion fermentation of lactic acid bacteria according to the present invention on the scalp of the subject.

BEST MODE

The present invention relates to a method for preparing an agent for prevention of hair loss and promotion of hair regrowth through a fusion fermentation process of lactic acid bacteria. The present invention provides a method for preparing an agent for prevention of hair loss and promotion of hair regrowth through fusion fermentation of lactic acid bacteria which comprises: (a) a step of blending aerobic lactic acid bacteria raw materials by blending *Lactobacillus*-genus 40 to 60 parts by weight and *Saccharomyces cerevisiae* 40 to 60 parts by weight, and diluting the blended raw materials with water where the blended raw materials are diluted to be 1 to 10 parts by weight based on the total amount with water; (b) a step of adding molasses into the aerobic lactic acid bacteria raw materials, where the molasses solution prepared by diluting 100 to 300 g of the molasses with 10 L of water is blended with the aerobic lactic acid bacteria raw materials; (c) a step of $1^{st}$ fermentation to prepare an aerobic lactic acid bacteria $1^{st}$ culture solution by fermenting the aerobic lactic acid bacteria raw materials blended with molasses at 15 to 35° C. for 10 to 15 days while introducing air thereto in an amount of 20 to 40 parts by weight per minute based on the total content of the aerobic lactic acid bacteria raw materials blended with molasses; (d) a step of a $1^{st}$ maturation to mature the aerobic lactic acid bacteria $1^{st}$ culture solution in a sealed state at 15 to 35° C. for 10 to 15 days; (e) a step of blending anaerobic lactic acid bacteria raw materials by blending *Weissella* sp 40 to 60 parts by weight and *Bifidobacterium* 40 to 60 parts by weight, and diluting the blended raw materials with water where the blended raw materials are diluted to be 1 to 10 parts by weight based on the total amount with water; (f) a step of adding molasses into the anaerobic lactic acid bacteria raw materials, where the molasses solution prepared by diluting 1 to 3 kg of the molasses with 10 L of water is blended with the anaerobic lactic acid bacteria raw materials; (g) a step of $1^{st}$ fermentation to prepare an anaerobic lactic acid bacteria $1^{st}$ culture solution by fermenting the anaerobic lactic acid bacteria raw materials blended with molasses at 15 to 35° C. for 10 to 15 days while introducing air thereto in an amount of 20 to 40 parts by weight per minute based on the total content of the anaerobic lactic acid bacteria raw materials blended with molasses; (h) a step of a $1^{st}$ maturation to mature the anaerobic lactic acid bacteria $1^{st}$ culture solution in a sealed state at 15 to 35° C. for 10 to 15 days; (i) a step of a $2^{nd}$ fermentation to prepare a $2^{nd}$ culture solution by mixing the $1^{st}$ matured aerobic lactic acid bacteria $1^{st}$ culture solution and the $1^{st}$ matured anaerobic lactic acid bacteria $1^{st}$ culture solution, blending the mixed solution with a molasses solution prepared by diluting 0.5 to 1.5 kg of molasses with 10 L of water, and with the mixed solution, and fermenting the mixed solution blended with the diluted molasses solution at 25 to 45° C. for 10 to 15 days while introducing air thereto in an amount of 20 to 40 parts by weight per minute based on the total content of the mixed solution blended with the diluted molasses solution; and (j) a step of a $2^{nd}$ maturation to mature the fermented $2^{nd}$ culture solution in a sealed state at 25 to 45° C. for 10 to 15 days.

Hereinafter, an embodiment of the method for preparing an agent for prevention of hair loss and promotion of hair regrowth through fusion fermentation of lactic acid bacteria according to the present invention will be described in detail with reference to the accompanying drawings.

The agent for prevention of hair loss and promotion of hair regrowth through fusion fermentation of lactic acid bacteria according to the present invention prevents hair from falling out and promotes hair regrowth to induce hair to grow thick and healthy, and contains 40 to 60 parts by weight of a microbial seed culture solution obtained by fusion fermentation with aerobic lactic acid bacteria and anaerobic lactic acid bacteria coexisting, 1 to 3 parts by weight of molasses and 40 to 60 parts by weight of purified water. Furthermore, fusion fermentation is to maintain a complex fermentation state in which anaerobic microorganisms and aerobic microorganisms coexist and activate each other to increase the density of existing microorganisms by hundreds of times or more.

In the present invention, aerobic lactic acid bacteria may include *Lactobacillus* and *Saccharomyces cerevisiae*. *Lactobacillus* (lactic acid bacteria) are bacteria that live in the human small intestine and produces a large amount of lactic acid by fermenting sugars to obtain energy. Morphologically, it is a gram-positive non-spore *bacillus* that shows polymorphism, and shows various forms from short rod to long rod, and there are also species that show Coryne type. *Lactobacillus* regulates the body's immunity and inflammation from harmful bacteria. It is an aerobic bacterium, but prefers to grow in an oxygen-less environment, and produces lactic acid from various sugars. *Lactobacillus* promotes fermentation, promotes hair health and hair growth by increasing the formation of anagen hair follicles, and has a high survival rate even at high temperatures due to its strong heat resistance.

*Saccharomyces cerevisiae* is a type of facultative anaerobic bacteria that can grow in both aerobic and anaerobic conditions, and is a so-called brewer's yeast. *Saccharomyces cerevisiae* promotes fermentation and grows well in the presence of free oxygen. It improves scalp health by preventing aging of the scalp, preventing hair loss or promoting hair growth, and produces organic acids and vitamins, and also serves as a protein source, along with the function of immunity and protection from harmful bacteria.

In addition, the anaerobic lactic acid bacteria may include *Weissella* and *Bifidobacterium*. *Weissella* is a fermenting lactic acid bacterium that is abundant in kimchi. The lactic acid bacteria of the genus *Weissella* have a high biofilm formation inhibitory effect, activate immune cells to increase immunity, and increase the concentration of interleukin, which has anti-obesity, anti-cancer, antibacterial and anti-inflammatory functions, as well as preventing the production of fat cells. Moreover, it is effective in skin improvement, wound treatment, and hair loss treatment.

*Bifidobacterium* is a lactic acid bacterium that lives in the human large intestine, and synthesizes vitamin B1, acidifies the pH inside the intestine to activate peristalsis and intestinal immunity, and inhibits the growth of other pathogens. *Bifidobacterium* promotes fermentation, suppresses the occurrence of atopic dermatitis by helping blood circulation, and has anti-cancer and hair loss prevention effects.

Furthermore, lactic acid bacteria of the genus *Lactobacillus* and lactic acid bacteria of the genus *Weissella*, represented by kimchi lactic acid bacteria, are vegetable lactic acid bacteria, and it has been confirmed that most survive even when exposed to gastric acid or bile acid. It is known to help colitis suppression, obesity suppression, antibacterial and antiviral action, immunity enhancement, stress relief, hair growth promotion, and making existing hair thicker. This is because kimchi lactic acid bacteria lower blood lipid levels and increase peripheral blood flow.

Microbial seed culture solution is prepared by fusion fermentation through the following steps of: adding an appropriate amount of ingredients selected from sugar, yeast, leaven, glucose and the like, which are food for microorganisms, into a culture vessel; sterilizing the culture vessel by heating at a high temperature and then cooling the container; adding microbial seeds of *Lactobacillus, Saccharomyces cerevisiae, Weissella*, and *Bifidobacterium*, respectively; and fermenting and culturing thereof for more than 15 days under anaerobic conditions, and then fermenting and culturing for more than 15 days under aerobic conditions. When the microbial seed culture solution is used, bacteria with different properties coexist with each other in the same environment, act jointly and share roles to further promote fermentation, and the efficiency of preventing aging of the scalp, preventing hair loss, and promoting hair growth can increase greatly. At this time, the total number of aerobic lactic acid bacteria included in the microbial seed culture solution may be 40 to 60%, and the total number of anaerobic bacteria may be 40 to 60%.

In addition, in the fermented pine needle extract, the main component of pine needles, turpentine, which is rich in unsaturated fatty acids, lowers cholesterol levels and expands peripheral blood vessels thereby facilitating blood circulation. Moreover, pine needles contain a large amount of nutrients such as vitamins A, C and K, calcium, iron, and chlorophyll, so they are effective in preventing anemia, senile dementia, and hair loss. The beta-carotene component of pine needles effectively removes active oxygen and helps prevent aging and various cancers. In addition, pine needles contain eight essential amino acids for the human body, and in particular, it is recorded in Herbal Medicine that pine needles grow hair.

Next, the method for preparing an agent for prevention of hair loss and promotion of hair regrowth through fusion fermentation of lactic acid bacteria according to the present invention will be described.
(Method for Preparing an Agent for Prevention of Hair Loss and Promotion of Hair Regrowth)
1. Raw Material Blending Step:

(1) As aerobic lactic acid bacteria, 40~60 parts by weight (preferably 45 to 55 parts by weight, most preferably 50 parts by weight) of *Lactobacillus* and 40~60 parts by weight (preferably 45 to 55 parts by weight, most preferably 50 parts by weight) of *Saccharomyces cerevisiae* were blended. Then, the blended raw materials were diluted with water, wherein the blended raw materials were blended in 1 to 10 parts by weight (preferably 5 parts by weight) compared to the total amount with water. That is, the blended raw materials were diluted with water at a ratio of 1:14 to 1:24 (preferably 1:19), and a total of 10.5 kg of aerobic lactic acid bacteria raw materials were mixed.

(2) As anaerobic lactic acid bacteria, 40~60 parts by weight (preferably 45 to 55 parts by weight, most preferably 50 parts by weight) of *Weissella* and 40~60 parts by weight (preferably 45 to 55 parts by weight, most preferably 50 parts by weight) of *Saccharomyces cerevisiae* were blended. Then, the blended raw materials were diluted with water, wherein the blended raw materials were blended in 1 to 10 parts by weight (preferably 5 parts by weight) compared to the total amount with water. That is, the blended raw materials were diluted with water at a ratio of 1:14 to 1:24 (preferably 1:19), and a total of 10.5 kg of anaerobic lactic acid bacteria raw materials were mixed.

At this time, the aerobic lactic acid bacteria raw material and the anaerobic lactic acid bacteria raw material were separated and blended in respective culture vessels.

2. Molasses Adding Step:

Molasses was added to each of the aerobic lactic acid bacteria raw material and the anaerobic lactic acid bacteria raw material separately blended in respective culture vessel and then blended, wherein molasses was blended in 1 to 3 parts by weight (preferably 2 parts by weight) relative to the total of the blended raw materials and molasses. 10.1 to 10.3 kg (preferably 10.2 kg) of molasses solution prepared by diluting 100 to 300 g (preferably 200 g) of molasses with 10 L of water was blended with each blended raw material to prepare a total of 20.7 kg of the mixed aerobic lactic acid bacteria raw material and the mixed anaerobic lactic acid bacteria raw material, respectively.

3. $1^{st}$ Fermentation Step:

The blended aerobic lactic acid bacteria raw material was fermented at 15 to 35° C. (preferably 20 to 30° C., more preferably 25° C.) for 10 to 15 days (preferably 13 days) while introducing air thereto in an amount corresponding to 20 to 40 parts by weight per minute based on the total content of the blended aerobic lactic acid bacteria raw materials (20.7 kg) to prepare an aerobic lactic acid bacteria $1^{st}$ culture solution.

Then, the blended anaerobic bacteria raw material was fermented at 15 to 35° C. (preferably 20 to 30° C., more preferably 25° C.) for 10 to 15 days (preferably 13 days) while introducing air thereto in an amount corresponding to 20 to 40 parts by weight per minute based on the total content of the blended anaerobic bacteria raw materials (20.7 kg) to prepare an anaerobic lactic acid bacteria $1^{st}$ culture solution.

4. $1^{st}$ Maturation Step:

The $1^{st}$ culture solution cultured by the $1^{st}$ fermentation of the aerobic lactic acid bacteria raw material and the $1^{st}$ culture solution cultured by the $1^{st}$ fermentation of the anaerobic lactic acid bacteria raw material were subjected to a $1^{st}$ maturation, respectively, in a sealed state at 15 to 35° C. (preferably 20 to 30° C., more preferably 25° C.) for 10 to 15 days (preferably 13 days).

5. Mixing and $2^{nd}$ Fermentation Step:

The $1^{st}$ culture solution of the $1^{st}$ matured aerobic lactic acid bacteria and the $1^{st}$ culture solution of the $1^{st}$ matured anaerobic lactic acid bacteria were placed in a prepared culture vessel capable of containing both and then mixed. Molasses solution was blended with the mixed solution of aerobic lactic acid bacteria and anaerobic lactic acid bacteria. The molasses solution was prepared by blending and diluting 0.5 to 1.5 kg (preferably 1 kg) of molasses with 10 L of water. In addition, the solution mixed with the molasses solution was fermented at 25 to 45° C. (preferably 35° C.) for 10 to 15 days (preferably 13 days) while introducing air thereto in an amount corresponding to 20 to 40 parts by weight per minute based on the total content of 52.4 kg to prepare a $2^{nd}$ culture solution.

6. $2^{nd}$ Maturation Step:

The secondarily fermented $2^{nd}$ culture solution was matured in a sealed state at 25 to 45° C. (preferably 35° C.) for 10 to 15 days (preferably 13 days) to prepare a $2^{nd}$ culture solution.

7. Mixing and $3^{rd}$ Fermentation Step:

The secondarily matured $2^{nd}$ culture solution and a fermented pine needle extract solution, which was prepared by diluting 0.1 to 1 kg (preferably 500 g) of a pine needle extract with 10 L of water based on the $2^{nd}$ culture solution and then fermenting thereof, were mixed. Then, the solution mixed with the fermented pine needle extract solution was fermented at 38 to 42° C. (preferably 40° C.) for 10 to 15 days (preferably 13 days) while introducing air thereto in an amount corresponding to 10 to 20 parts by weight per minute based on the total content of 62.9 kg to prepare a $3^{rd}$ culture solution. The fermented pine needle extract solution was prepared by mixing 40 to 60 parts by weight of a pine needle extract and 40 to 60 parts by weight of molasses and maturing in a sealed state at 15 to 35° C. (preferably 25° C.) for 120 to 180 days (preferably 150 days).

8. $3^{rd}$ Maturation Step:

The tertiarily fermented culture solution was matured in a sealed state at 38 to 42° C. (preferably 40° C.) for 10 to 15 days (preferably 13 days) to prepare a $3^{rd}$ culture solution.

Example 1

The culture solution, which was prepared by repeating cycles of fermentation, decomposition, and synthesis by fusion fermentation of aerobic lactic acid bacteria and anaerobic lactic acid bacteria by using the method for preparing an agent for prevention of hair loss and promotion of hair regrowth through fusion fermentation of lactic acid bacteria according to the present invention, was applied to several subjects to test hair growth.

First, after sufficiently wetting the hair of the subjects with warm water, the agent for prevention of hair loss and promotion of hair regrowth prepared according to the present invention was applied to the hair and made bubbles, and then the hair was washed with warm water.

Then, the scalp was acupressure using a brush, and once again, the agent for prevention of hair loss and promotion of hair regrowth through fusion fermentation of lactic acid bacteria prepared according to the present invention was applied to the hair of the subjects, and then the same operation was repeated.

As described above, using the agent for prevention of hair loss and promotion of hair regrowth prepared according to the present invention, the subject's hair was shampooed three times a day, morning, evening and before bed.

In the above, the subject was made to use the agent for prevention of hair loss and promotion of hair regrowth prepared according to the present invention, and the hair growth condition and scalp condition of the subject after a certain period of time are shown in FIG. 3 by time. As can be seen from the hair growth condition and scalp condition of the subject shown in FIG. 3, the hair growth condition of the subject was confirmed for 1 month, 3 months, and 5 months, respectively, from the hair growth condition before the procedure, and it was clearly seen with the naked eye that hair growth occurred in the hair loss area due to the use of the agent for prevention of hair loss and promotion of hair regrowth prepared according to the present invention.

Example 2

In addition, the agent for prevention of hair loss and promotion of hair regrowth of the present invention was administered to 50 people (27 males, 23 females) with ongoing hair loss for 5 months from January to take 150 mL of the agent for prevention of hair loss and promotion of hair regrowth twice a day, morning and evening, on an empty stomach. As a result, after 5 months of taking the agent for prevention of hair loss and promotion of hair regrowth, there was a statistically significant increase in the number and thickness of hair, with the number of hairs per 1 cm² of scalp area increasing from an average of 75.27 to 86.24.

Finally, it was found that the agent for prevention of hair loss and promotion of hair regrowth through fusion fermentation of lactic acid bacteria according to the present invention, which is prepared by repeating cycles of fermentation, decomposition, and synthesis through fusion fermentation of aerobic lactic acid bacteria and anaerobic lactic acid bacteria, prevents hair from falling off the scalp or hair becoming sparse or thinning when applied to the scalp, and prevents side effects that cause scalp troubles, thereby implanting the growth of healthy hair by promoting the delay of the hair cycle from the anagen phase to the catagen phase.

The above embodiment in the present invention is an example, and the present invention is not limited thereto. Anything having substantially the same configuration as the technical concept described in the claims of the present invention and achieving the same operational effect is included in the technical scope of the present invention.

INDUSTRIAL APPLICABILITY

The method for preparing an agent for prevention of hair loss and promotion of hair regrowth through fusion fermentation of lactic acid bacteria is characterized in that, by repeating cycles of fermentation, decomposition, and synthesis through fusion fermentation of aerobic lactic acid bacteria and anaerobic lactic acid bacteria to maximize active ingredients for preventing hair loss and promoting hair regrowth, it prevents hair from falling off the scalp or hair becoming sparse or thinning when applied to the scalp, and prevents side effects that cause scalp troubles by fermented and aged lactic acid bacteria mixed solution, thereby implementing the growth of healthy hair by promoting the delay of the hair cycle from the anagen phase to the catagen phase.

The invention claimed is:

1. A method for preparing an agent for prevention of hair loss and promotion of hair regrowth, wherein the method comprises a fusion fermentation of lactic acid bacteria comprising the steps of:
   (a) blending aerobic lactic acid bacteria raw materials by combining *Lactobacillus* sp. in an amount of 40 to 60 parts by weight with *Saccharomyces cerevisae* in an amount of 40 to 60 parts by weight, and diluting the combined raw materials with water such that the raw materials constitute 1 to 10 parts by weight of the total mixture;
   (b) adding molasses to the aerobic lactic acid bacteria raw materials by blending the raw materials with a molasses solution prepared by diluting 100 to 300 g of molasses in 10 L of water;
   (c) performing a first aerobic fermentation of the mixture obtained in step (b) at 15 to 35° C. for 10 to 15 days while introducing air into the mixture at 20 to 40 parts by weight per minute based on the total content of the mixture, thereby obtaining an aerobic lactic acid bacteria first culture solution;

(d) maturing the aerobic lactic acid bacteria first culture solution in a sealed state at 15 to 35° C. for 10 to 15 days;
   (e) blending anaerobic lactic acid bacteria raw materials by combining *Weissella* sp. in an amount of 40 to 60 parts by weight with *Bifidobacterium* sp. in an amount of 40 to 60 parts by weight, and diluting the combined raw materials with water such that the raw materials constitute 1 to 10 parts by weight of the total mixture;
   (f) adding molasses to the anaerobic lactic acid bacteria raw materials by blending the raw materials with a molasses solution prepared by diluting 1 to 3 kg of molasses in 10 L of water;
   (g) performing a first anaerobic fermentation of the mixture obtained in step (f) at 15 to 35° C. for 10 to 15 days while introducing air into the mixture at 20 to 40 parts by weight per minute based on the total content of the mixture, thereby obtaining an anaerobic lactic acid bacteria first culture solution;
   (h) maturing the anaerobic lactic acid bacteria first culture solution in a sealed state at 15 to 35° C. for 10 to 15 days;
   (i) performing a second fermentation to prepare a mixed culture solution by mixing the matured aerobic lactic acid bacteria first culture solution with the matured anaerobic lactic acid bacteria first culture solution, blending the mixed culture solution with a molasses solution prepared by diluting 0.5 to 1.5 kg of molasses in 10 L of water, and fermenting the mixture at 25 to 45° C. for 10 to 15 days while introducing air into the mixture at 20 to 40 parts by weight per minute based on the total content of the mixture; and
   (j) maturing the fermented mixed culture solution in a sealed state at 25 to 45° C. for 10 to 15 days.
2. The method according to claim 1, further comprising the steps of:
   (k) performing a third fermentation to prepare a third culture solution by mixing the matured mixed culture solution with a fermented pine needle extract solution prepared by diluting 0.1 to 1 kg of pine needle extract in 10 L of water and fermenting the diluted extract, and fermenting the resulting mixture at 38 to 42° C. for 10 to 15 days while introducing air into the mixture at 10 to 20 parts by weight per minute based on the total content of the mixture; and
   (l) maturing the fermented third culture solution in a sealed state at 38 to 42° C. for 10 to 15 days.
3. The method according to claim 2, wherein the fermented pine needle extract solution is prepared by mixing a pine needle extract in an amount of 40 to 60 parts by weight with molasses in an amount of 40 to 60 parts by weight, and maturing the mixture in a sealed state at 15 to 35° C. for 120 to 180 days.
4. An agent for prevention of hair loss and promotion of hair regrowth, wherein the agent is prepared by the method according to claim 1.

* * * * *